(12) United States Patent
Cantor

(10) Patent No.: US 7,569,025 B2
(45) Date of Patent: Aug. 4, 2009

(54) METHODS AND DEVICES FOR TREATING SEVERE PERIPHERAL BACTERIAL INFECTIONS

(75) Inventor: Tom L. Cantor, El Cajon, CA (US)

(73) Assignee: Scantibodies Laboratory, Inc., Santee, CA (US)

( * ) Notice: Subject to any disclaimer, the term of this patent is extended or adjusted under 35 U.S.C. 154(b) by 1084 days.

(21) Appl. No.: 10/405,974

(22) Filed: Apr. 1, 2003

(65) Prior Publication Data

US 2004/0024343 A1 Feb. 5, 2004

Related U.S. Application Data

(60) Provisional application No. 60/369,692, filed on Apr. 2, 2002.

(51) Int. Cl.
*A61M 37/00* (2006.01)
*C02F 1/44* (2006.01)
*A61K 9/16* (2006.01)

(52) U.S. Cl. .............. 604/5.04; 210/645; 210/690; 210/500.24; 424/489; 424/490; 424/164.1

(58) Field of Classification Search ............. 210/600, 210/634, 641, 644, 645, 739, 200, 322, 416.1, 210/500.1, 502.1, 506, 503, 504; 604/4.01, 604/5.04, 6.09, 6.11; 424/150.1, 163.1, 164.1, 424/165.1, 243.1, 244.1, 484, 400, 486, 489, 424/490, 497

See application file for complete search history.

(56) References Cited

U.S. PATENT DOCUMENTS

| | | | |
|---|---|---|---|
| 4,267,053 A | 5/1981 | Hashino et al. | |
| 4,375,414 A | 3/1983 | Strahilevitz | |
| 4,381,004 A * | 4/1983 | Babb | 604/5.02 |
| 4,576,928 A | 3/1986 | Tami et al. | 502/404 |
| 4,612,122 A | 9/1986 | Ambrus et al. | 210/638 |
| 4,620,977 A | 11/1986 | Strahilevitz | |
| 4,637,880 A | 1/1987 | Halbert | |
| 4,637,994 A | 1/1987 | Tani et al. | |
| 4,714,556 A | 12/1987 | Ambrus et al. | 210/638 |

(Continued)

FOREIGN PATENT DOCUMENTS

WO WO-91/01749 2/1991

(Continued)

OTHER PUBLICATIONS

International Search Report for PCT/US03/09890, mailed on Apr. 8, 2004, 5 pages.

(Continued)

*Primary Examiner*—Leslie R Deak
(74) *Attorney, Agent, or Firm*—Morrison & Foerster LLP

(57) ABSTRACT

The present invention relates to novel methods and devices for treating severe bacterial infections, such as septicemia, using an extracorporeal adsorption container. The device has a solid support disposed and confined within the container and a binding means associated with the solid support that is specific for affixing an infecting bacterium that is causing the severe peripheral bacterial infection and/or bacterial toxins from the bacterium. By passing the infected blood through the container. at least a portion of the infecting bacterium and/or bacterial toxins are removed. The treated blood is returned to the patient.

26 Claims, 15 Drawing Sheets

U.S. PATENT DOCUMENTS

| | | | |
|---|---|---|---|
| 4,737,544 A * | 4/1988 | McCain et al. | 424/443 |
| 4,787,974 A | 11/1988 | Ambrus et al. | 210/321.8 |
| 4,813,924 A | 3/1989 | Strahilevitz | |
| 4,824,432 A | 4/1989 | Skurkovich et al. | 604/4 |
| 5,179,018 A | 1/1993 | Bogard, Jr. et al. | 530/388.15 |
| 5,211,850 A | 5/1993 | Shettigar et al. | |
| 5,277,820 A | 1/1994 | Ash | |
| 5,437,861 A | 8/1995 | Okarma et al. | |
| 5,474,772 A | 12/1995 | Maddock | |
| 5,523,096 A | 6/1996 | Okarma et al. | |
| 5,536,412 A | 7/1996 | Ash | |
| 5,626,843 A | 5/1997 | Skurkovich et al. | |
| 5,730,713 A | 3/1998 | Okarma et al. | |
| 5,753,227 A | 5/1998 | Strahilevitz | |
| 5,773,384 A | 6/1998 | Davankov et al. | 502/402 |
| 5,817,045 A | 10/1998 | Sever, Jr. | |
| 5,855,782 A | 1/1999 | Falkenhagen et al. | |
| 5,888,511 A | 3/1999 | Skurkovich et al. | |
| 5,919,369 A | 7/1999 | Ash | |
| 6,039,946 A | 3/2000 | Strahilevitz | 424/140.1 |
| 6,046,225 A | 4/2000 | Maddock | |
| 6,077,499 A | 6/2000 | Griffiths et al. | |
| 6,090,292 A * | 7/2000 | Zimmermann et al. | 210/690 |
| 6,193,681 B1 * | 2/2001 | Davidner et al. | 604/6.08 |
| 6,210,677 B1 | 4/2001 | Bohannon | |
| 6,264,623 B1 | 7/2001 | Strahilevitz | |
| 6,287,516 B1 | 9/2001 | Matson et al. | 422/44 |
| 6,528,057 B1 | 3/2003 | Ambrus et al. | |
| 6,569,112 B2 | 5/2003 | Strahilevitz | |
| 6,602,502 B1 | 8/2003 | Strahilevitz | |
| 6,676,622 B2 | 1/2004 | Strahilevitz | |
| 6,730,266 B2 | 5/2004 | Matson et al. | |
| 6,736,972 B1 | 5/2004 | Matson | |
| 6,774,102 B1 | 8/2004 | Bell et al. | |
| 6,881,408 B1 | 4/2005 | Heinrich et al. | |
| 7,011,812 B1 | 3/2006 | Griffiths et al. | |
| 7,166,295 B1 | 1/2007 | Strahilevitz | |
| 2002/0019603 A1 | 2/2002 | Strahilevitz | |
| 2002/0064529 A1 | 5/2002 | Bohannon | |
| 2003/0232011 A1 | 12/2003 | Griffiths et al. | |
| 2004/0096821 A1 | 5/2004 | Keenan et al. | |
| 2004/0120965 A1 | 6/2004 | Bohannon | |
| 2004/0161736 A1 | 8/2004 | Bristow | |
| 2004/0220508 A1 | 11/2004 | Strahilevitz | |
| 2005/0103712 A1 | 5/2005 | Voyce | |
| 2006/0292162 A1 | 12/2006 | Buckheit, Jr. | |

FOREIGN PATENT DOCUMENTS

| | | |
|---|---|---|
| WO | WO-95/03084 | 2/1995 |
| WO | WO-00/23792 | 4/2000 |
| WO | WO-02/30474 | 4/2002 |

OTHER PUBLICATIONS

Aethlon Medical Inc. Corporate Overview, printed from website address http://www.corporate-ir.net/ireye/content_alone.zhml?ticker=AEMD&script=2100&layou..., print date May 19, 2005.

Alibek and Bailey, The Application of the Aethlong Medical Hemopurifier™ in Biodefense (2004), printed from website address www.aethlonmedical.com, print date May 19, 2005.

U.S. Appl. No. 10/712,662, filed by Brian Voyce on Nov. 13, 2003.

Office Action mailed on Sep. 21, 2005, from U.S. Appl. No. 10/712,662.

Declaration of Thomas L. Cantor, dated Dec. 10, 2005.

Martin, "AIDS filter may remove virus from blood," United Press International, Apr. 28, 2001.

Business Wire, "Aethlon Medical Announces New Patent Issuance; Method for Removal of HIV and Other Viruses From Blood," Mar. 12, 2003.

Immunoassay, Diamandis and Christopoulos, (eds.) Academic Press, San Diego, CA, (1996) pp. 216-222.

Jaber et al., American Journal of Kidney Diseases (1997) 30(5):S44-S56.

Shoji, Therapeutic Apheresis and Dialysis (2003) 7:108-114.

Devlin, ed., Textbook of Biochemistry with Clinical Correlations, $5^{th}$ ed., (2001) p. 4.

Foster, J. Clinical Investigation (2004) 114(12):1693-1696.

Powledge, PLoS Biology (2004) 2(2):151-154.

Schroeder, American Family Physician (2005) 71(5):921-928.

International Search Report and Written Opinion for PCT/US06/23553, mailed Aug. 12, 2008, 6 pages.

* cited by examiner

FIGURE 3

The Antibiotic Strategy

Advantages

1. Anthrax is easy to kill. (Cipro, Doxycycline, etc.)
2. Curable if antibiotics used in primary phase.

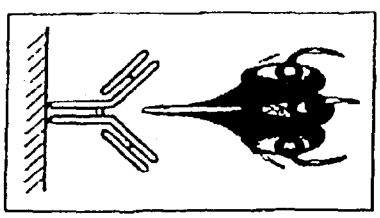

Disadvantages

Minor

1. Some side effects.
2. Incomplete course of treatment may result in selection of a resistant strain.

Major

1. Ineffective against Toxins*, the actual cause of death. "Patients die with sterile blood."
2. Ineffective against genetically modified strains*.
3. Dangerous to use in secondary phase because they accelerate death by causing rapid toxin release.
4. Ineffective against resistant strains*.

FIGURE 6
Typical Appearance of EBTR Units
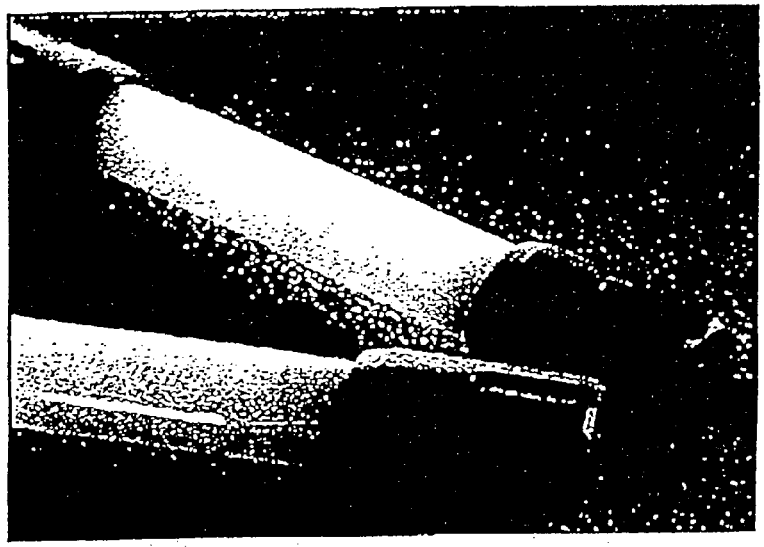
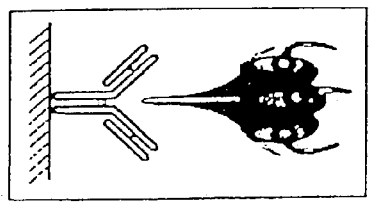

FIGURE 7

Use of EBTR

When
A patient has reached the clinical secondary phase of anthrax infection

And
The assay values of the bacteria, PA, EF and LF tests have confirmed secondary phase levels

Then (Bacteria, EF, LF, PA)

300ml/hr PUMP

Until
The assay values of the bacteria, PA, EF and LF tests have confirmed:
 a) it is safe to use antibiotics as a mop-up or
b) the immune system is able to overcome the residual infection or clear the residual toxins.

FIGURE 8

Patient Selection for EBTR

Patient selection would be based on:

a) Clinical symptoms indicating secondary phase of infection alternatively or in conjunction with b) Rapid quantitative blood assays (objective evaluation) for bacillus and/or toxins reaching thresholds (i.e. approaching LD50 levels) based on the level of bacteria at which the use of antibiotics puts the patient at risk through release of a flood of toxins

FIGURE 9

EBTR Treatment

1. Patient is injected I.V. with 100 units heparin/kg body weight.

2. EBTR unit is removed from its sterile, sealed package.

3. Inlet silicone tubing (bottom of column) is placed in a 100-300 ml peristaltic blood pump (battery or AC powered unit for field deployable use).

4. 14 gauge needle is inserted into the brachial vein and shutoff valves are opened.

5. Pump speed is increased to 100 ml/minute.

6. EBTR unit is filled with blood and rotated to expel any trapped air.

7. When blood has filled the unit, an outlet line 14 gauge outlet needle is inserted into the patient's other brachial vein.

8. Pump speed is increased to 300 ml/minute.

FIGURE 10

EBTR Treatment Monitoring

During the EBTR treatment, blood levels of the bacillus and its toxins are assayed to determine the point when either (a) antibiotics may be used safely as a mopping up procedure without risk of toxin overload, or (b) the immune system may be able to clear residual bacteria and toxins.

Disposition of EBTR Unit

After use, the EBTR unit is incinerated

FIGURE 11

Functional Capacity of One Gram of Affinity-Purified Antibody for Lethal Toxin 1. Activity of Lethal Toxin 235 units per mg protein Vick, et.al. 1968. "Neurological and Physiological Responses of the Primate to Anthrax Toxin."
    J Infect Diseases 118:85-96.

2. Lethal Dose 1.85 units per gm body weight for primates

Vick, et.al. 1968. "Neurological and Physiological Responses of the Primate to Anthrax Toxin."
    J Infect Diseases 118:85-96.

150 lb. human = 68,182 gms x 1.85 =
    126,263 units / 235 units / mg = 537 mgs 3. Molecular weight of Lethal Toxin =
   93,000 (LF) + 90,000 (PA) = 183,000 therefore, 537 mgs = $1.77 \times 10^{18}$ molecules 4. 1 gm of anti-Lethal Factor antibody (m.w. = 155,000) =
   $3.89 \times 10^{18}$ antibody molecules 5. Therefore, there are 2.2 times excess antibodies

FIGURE 12

Functional Capacity of One Gram of Affinity-Purified Antibody for Bacillus Anthracis 1. Expired guinea pig had $10^{8.8}$ organisms per gm of whole body tissue (Figure $10^9$)

2. 150 lb. human weighs 68,181 gms - when expired, corresponds to $6.82 \times 10^{13}$ organisms 3. 1 gm of anti Bacillus Anthracis antibody (m.w. = 155,000) = $3.89 \times 10^{18}$ antibody molecules 4. Therefore, there are 57,000 antibody molecules for each Bacillus Anthracis organism

Preliminary Composition of EBTR 1. 0.4 gm anti Lethal Factor Antibody 2. 0.2 gm anti Edema Factor Antibody 3. 0.2 gm anti Protective Antigen Antibody 4. 0.2 gm anti Bacillus Anthracis Antibody

EBTR

Antibody Leaching Control

1. Following production, each EBTR unit is thoroughly washed with alternating high and low pH solutions and finally rinsed and stored in isotonic saline solution.

2. The final isotonic saline solution rinse is assayed for goat IgG with an immunoassay sensitive to 10 picograms/mL.

FIGURE 14

EBTR

Major Advantages over Antibiotics 1. (Effective against toxins)   whereas antibiotics are not.

2. (Effective against genetically-modified strains)
   whereas antibiotics are not.

3. (Does not accelerate death by causing rapid toxin release)
   whereas antibiotics do.

4. (Effective against resistant strains)
   whereas antibiotics are not.

5. Action is more rapid than antibiotics (i.e. in 15 minutes, total body blood can be immuno-cleansed).

FIGURE 15

Application of EBTR to Septicemia

1. The Incidence

> 300,000 cases in the U.S.A. of Septicemia per year
    14,000 cases in New York City alone in 1995
    Increasing by 140% per year 2. Mortality > 50,000 deaths per year in the U.S.A. are caused by Septicemia
    13th leading cause of death in the U.S.A.

3. Costs

In 1995, a study in New York city hospitals of Staphylococcus A Septicemia found that each case cost...

$32,000/case to treat Staphylococcus A Septicemia
    For U.S.A. > $10 billion/year 4. Greatest Need Multiple Resistant Staphylococcus A

METHODS AND DEVICES FOR TREATING SEVERE PERIPHERAL BACTERIAL INFECTIONS

CROSS REFERENCE TO RELATED APPLICATIONS

This application claims priority to Provisional Patent Application Ser. No. 60/369,692 filed Apr. 2, 2002 under 35 U.S.C. § 119(e). The disclosure of the above-referenced application is incorporated in its entirety by reference.

TECHNICAL FIELD

The present invention relates to novel methods and devices for treating severe bacterial infections, such as septicemia or bacteremeia, using an extracorporeal adsorption container. The device has a solid support disposed and confined within the container and a binding means associated with the solid support that is specific for affixing an infecting bacterium that is causing the severe peripheral bacterial infection and/or bacterial toxins from the bacterium. By passing the infected blood through the container, at least a portion of the infecting bacterium and/or bacterial toxins are removed. The treated blood is returned to the patient.

BACKGROUND ART

Bacterial infections are becoming a greater danger. Certain bacteria have become resistant to antibiotic treatment, in some cases to a number of antibiotics, either naturally or through genetic manipulation. Septicemia is now among the most common causes of death in the United States of America ($13^{th}$ as of the year 2000), accounting for over ten billion dollars annually in health care costs. Fatality rates for septicemia are around 20%, totaling over 50,000 deaths annually.

In some cases a bacterium infects a person in a manner that makes any infection dangerous. Inhalation anthrax (*bacillus anthracis*) infection can be such a case. If inhaled, anthrax spores can cause a set of non-specific symptoms (malaise, fatigue, myalgia, and fever) that do not lead to a clinical diagnosis of anthrax infection, absent actual knowledge of an anthrax exposure having taken place. The spores are deposited in the alveolar spaces and transported to mediastinial lymph nodes by lymphatic action. Once in the nodes, the spores can transform to vegetative cells. With germination, disease follows rapidly into a severe peripheral bacterial infection.

Replicating bacterium can release toxins that lead to necrosis, edema, and hemorrhage. (For the purposes of the present invention, toxins can also refer to any factors that lead to an actual toxin, such as anthrax edema factor (EF a 89 kD adenylate cyclase protein) that leads to edema toxin (ET) if combined with anthrax protective antigen (PA, a 83 kD cell binding component) or anthrax lethal factor (LF, a 90 kD metalloprotease) which leads to lethal toxin (LT) if combined with PA.) At this point, diagnosis typically does not save the patient. In fact, antibiotic treatment may actually cause a crisis in the blood that leads to death, by killing the infecting bacteria, and thereby releasing a flood of toxins to the peripheral system, a toxin overload.

Extracorporeal devices have been used in the past, but not for treating patients for severe peripheral bacterial infections. For example, U.S. Pat. No. 6,039,946 to Strahilevitz discloses an extracorporeal affinity adsorption device for providing therapeutic intervention. The container contains a chelant for binding metal ions in the blood and an antibody specifically binding to either an anti-cancer drug or a combined anti-cancer drug/targeting antibody.

Extracorporeal devices have also been disclosed for use in the treatment of retroviral diseases such as HIV infection; U.S. Pat. No. 4,824,432 teaches about a container that has a means for removing interferon or HIV virus.

DISCLOSURE OF THE INVENTION

The present invention relates to novel methods and devices for treating severe bacterial infections using an extracorporeal adsorption container. The device has a solid support disposed and confined within the container and a binding means associated with the solid support that is specific for affixing an infecting bacterium that is causing the severe peripheral bacterial infection and/or bacterial toxins from the bacterium. By passing the infected blood through the container, at least a portion of the infecting bacterium and/or bacterial toxins are removed. The treated blood is returned to the patient, whether it is a human or an animal.

In particular, the emergency bacterium and/or toxin removal (EBTR) device for treating a patient having a sever peripheral bacterial infection comprises an extracorporeal adsorption container having an inlet means and an outlet means for circulating blood in a whole or separated form. A solid support is disposed and confined within the container. A binding means is associated with the solid support that is specific for affixing an infecting bacterium that is causing a severe peripheral bacterial infection, thereby allowing for the removal of at least a portion of the infecting bacterium and the return of the treated blood to the patient. For the purposes of the present invention, "severe peripheral bacterial infection" includes the patient having a level of either a bacterium or a mycobacterium in the peripheral system that the use of an antibiotic at that stage of infection puts the patient at a significant risk of induced bacteremia or septicemia from the killing of the infecting bacterial load and/or the peripheral levels of associated bacterial toxins, and also includes the patient having a level of bacterium that is antibiotic resistant, either from environmental exposure or genetic manipulation of the bacterium or mycobacterium. The term also refers to such infections wherein the level of toxins released from the infecting microbe have reached a stage where the patient is at risk from the effects of the toxin on the body, including hemorraghic or edemic destruction of cells. Examples of severe peripheral bacterial infections include an infecting microbe (bacterium or mycobacterium) from the *bacillus, meningococcus, streptococcus, staphylococcus,* or *paratuberculosis* species. The detection of bacterial infections can be determined by a number of conventional diagnostic means.

A variety of conventional solid supports are suitable for the present invention, including coated beads, hollow fibers, or membranes. Typically, one should use a support capable of holding a large load of binding means, preferably enough to remove at least one mg of bacteria. The support preferably has a surface area to volume ratio of at least about 4 to 1. For convenience, one can size the container so as to provide enough binding capacity to remove a predetermined amount of bacteria from the patient, enabling the treating physician to estimate the number of containers necessary to treat an assayed level of infection.

The binding means also can be conventional means for binding to an infecting bacterium and/or associated toxins. Typically, the binding means is adsorbed or bonded to the solid support in an amount sufficient to remove at least 1 mg of infecting bacterial or the associated toxins. Suitable binding means include immunoadsorbents such as Con A, lectins, monoclonal antibodies, or polyclonal antibodies. In certain embodiments one can combine at least two different binding means together in one container, such as either binding means for two separate bacterium or for a bacterium and at least one toxin produced by that bacterium. Alternatively, one can provide for a series of containers, each with a separate binding means. In that vein, one can provide for containers that can attach to each other in a serial fashion. For example, each end can be provide with a threaded inlet or outlet port so that a container containing a binding means for a bacterium can be threaded onto a container for the associated bacterial toxins, if desired.

An object of the present invention also is to provide for methods for treating a patient having a severe peripheral bacterial infection. The first step is to connect an extracorporeal adsorption container as described above to the patient's peripheral system. The patient's blood is circulated through the container, thereby cleansing the blood by removing at least a portion of the infecting bacterium and/or the associated bacterial toxins. The treated blood is returned to the patient. Typically, the blood is treated until the bacterial load has been reduced to a level such that the use of an antibiotic does not put the patient at a significant risk of induced bacteremia or septicemia. To speed up the patient recovery and reduce the risk of bacterial overload, one can pump the blood through the extracorporeal container.

In some cases, it is preferred to monitor the blood for either the reduction in the level of bacteria or the associated toxins after a set treatment period. Also, any antibiotic treatment of the patient should be curtailed until the infecting bacterial load has been lowered to an acceptable risk level. One should avoid inducing bacterial toxin overload by killing bacterium and thereby releasing a flood of toxins.

BRIEF DESCRIPTION OF THE DRAWINGS

FIG. 3 illustrates the Antibiotic Strategy.
FIG. 6 illustrates the Typical Appearance of EBRT Units.
FIG. 7 illustrates the Use of EBTR.
FIG. 8 illustrates the Patient Selection for EBTR.
FIG. 9 illustrates the EBTR Treatment.
FIG. 10 illustrates the EBTR Treatment Monitoring.
FIG. 11 illustrates the Functional Capacity of One Gram of Affinity-Purified Antibody for Lethal Toxin
FIG. 12 illustrates the Functional Capacity of One Gram of Affinity-Purified Antibody for Bacillus Anthracis
FIG. 14 illustrates the EBTR Major Advantages over Antibiotics.
FIG. 15 illustrates the Application of EBTR to Septicemia.

BEST MODES FOR CARRYING OUT THE INVENTION

Figure 1:
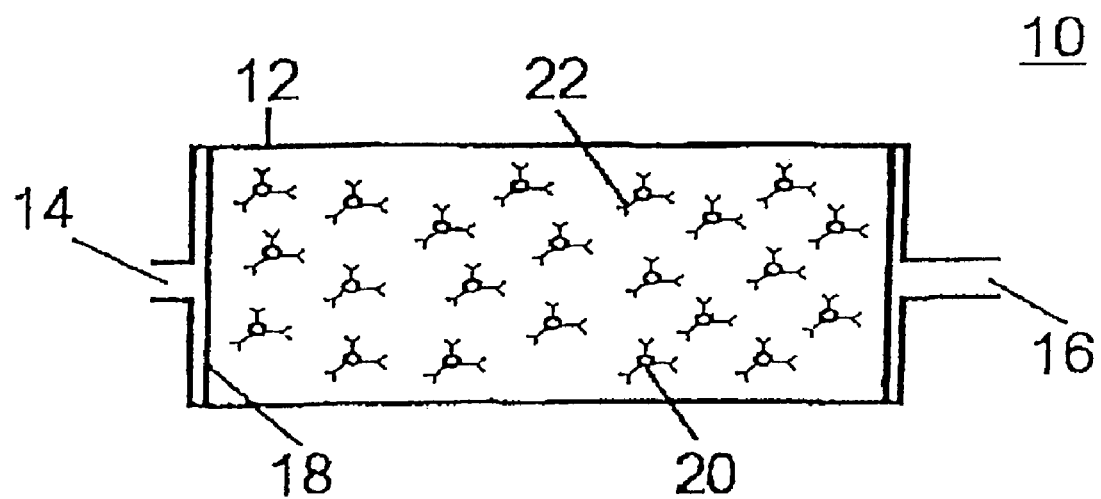
FIG. 1 is a sectional view of the extracorporeal container of the present invention.
Figure 2:
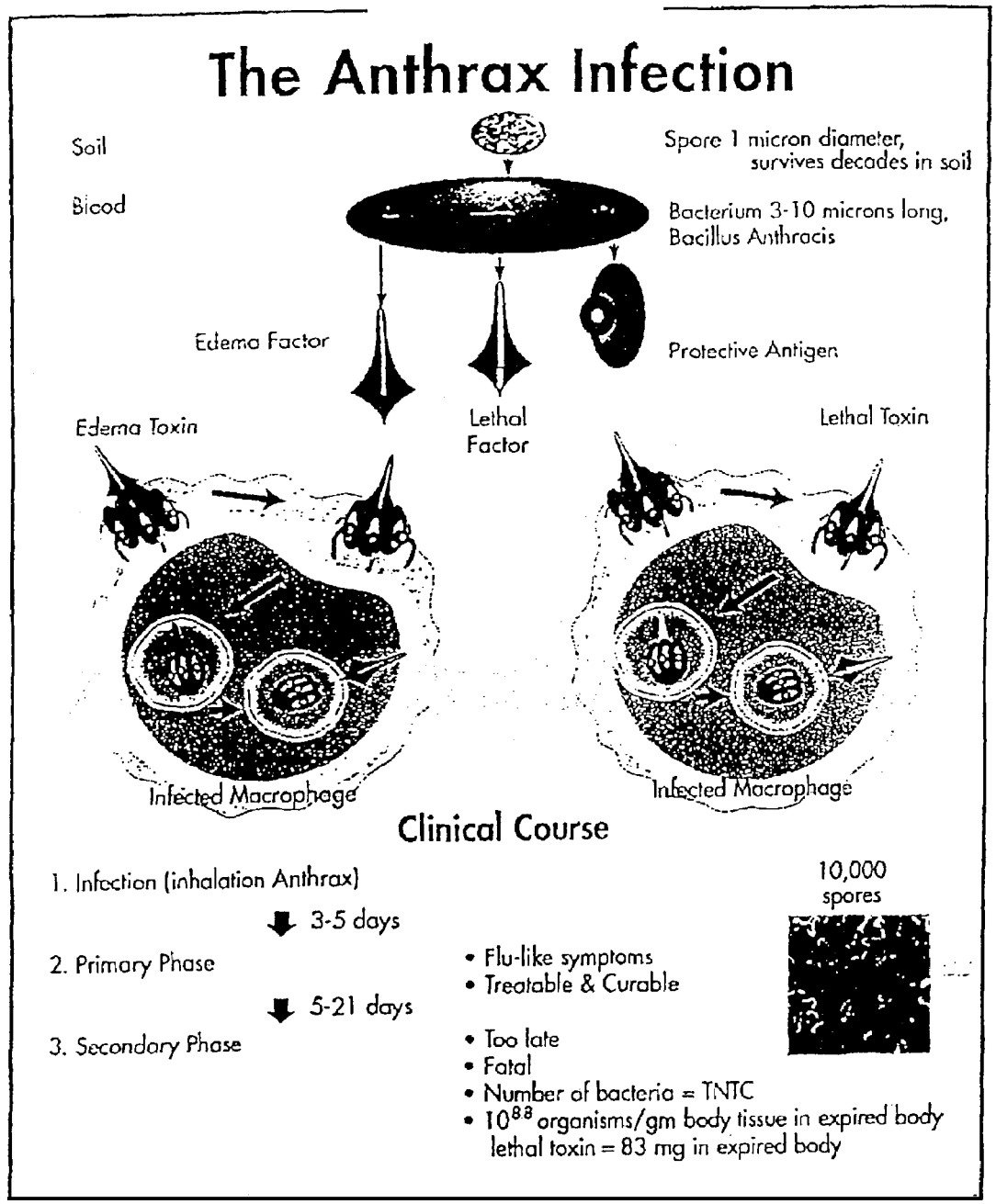
FIG. 2 illustrates the Anthrax Infection.
Figure 4:
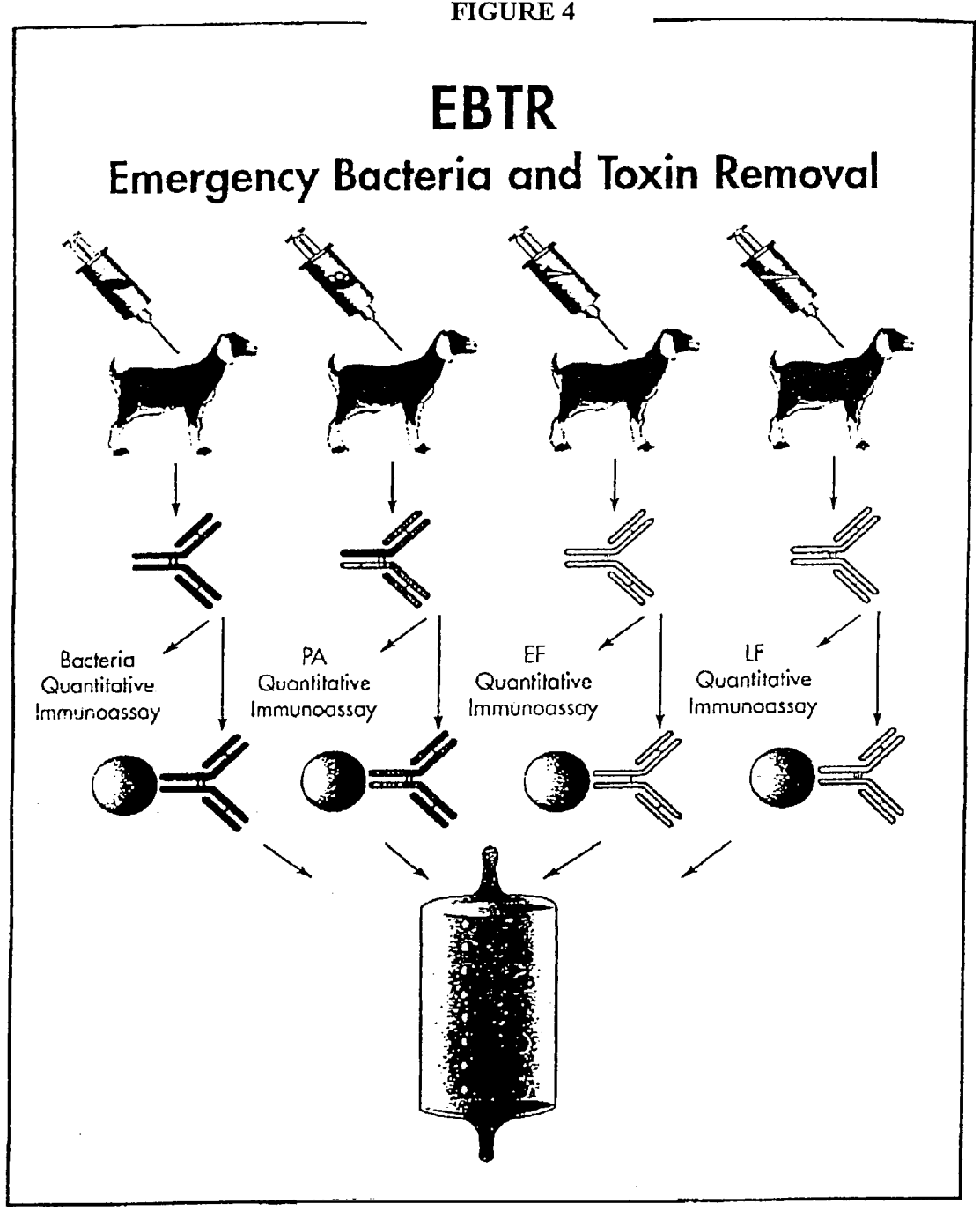
FIG. 4 illustrates the EBTR Emergency Bacteria and Toxin Removal.
Figure 5:
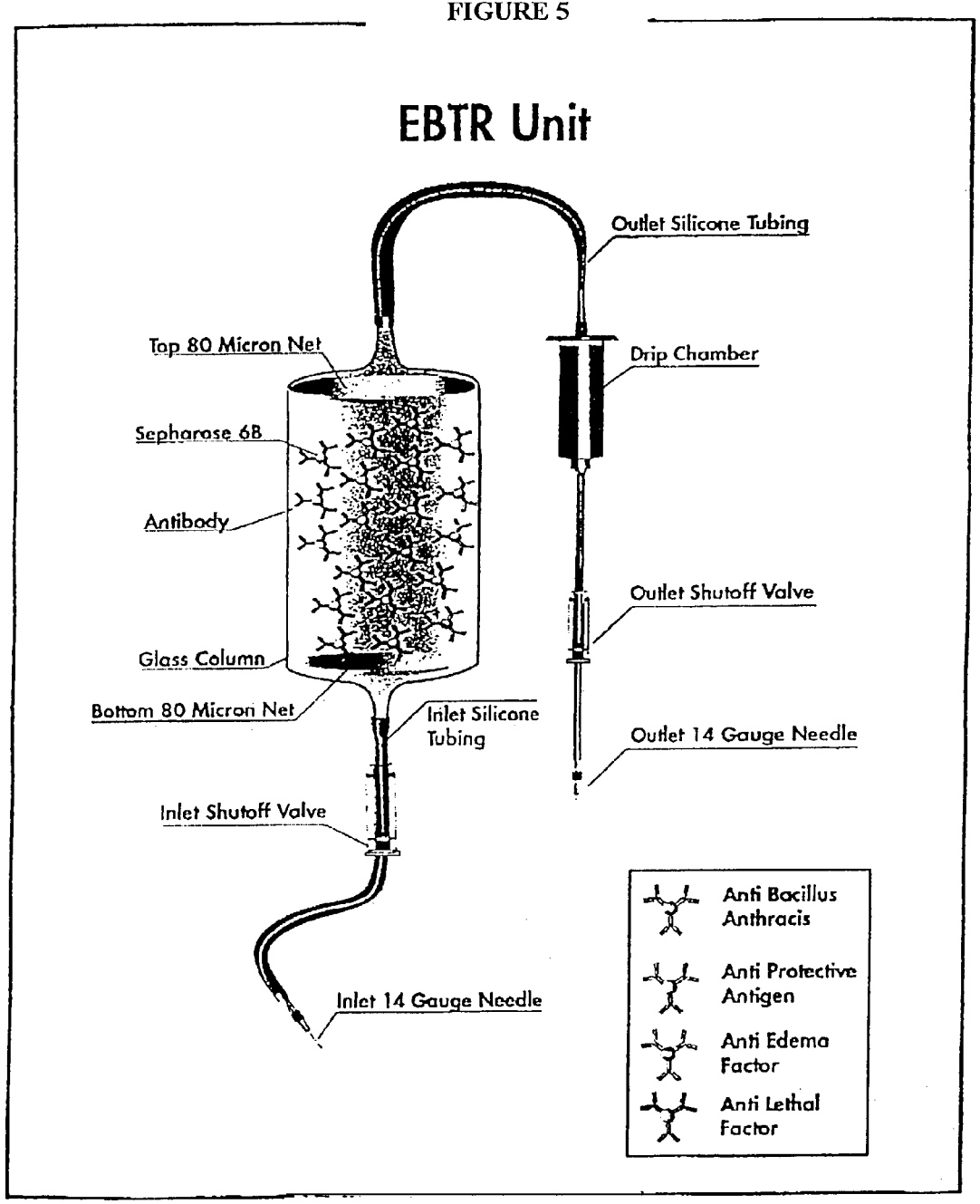
FIG. 5 illustrates the EBTR Unit.
Figure 13:
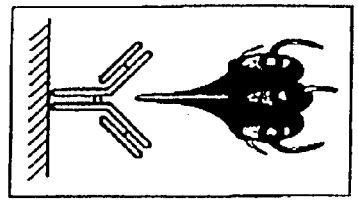
FIG. 13 illustrates the EBTR Antibody Leaching Control.

Description of an EBTR Unit
A preferred embodiment of the extracorporeal adsorption container (10) used in the present invention is shown in the FIGURE. A disposable glass or polypropylene column (12) has a conventional inlet fitting (14) at the proximal end and a conventional outlet fitting (16) at the distal end. Medical grade silicon tubing can be connected to each end. The inlet end can have affixed to it a shutoff valve and a first 14 gauge hypodermic needle. The end of the outlet silicone tubing can have connected to it a blood administration set and a shutoff valve and a second 14 gauge needle.

Inside of the column is the bacterium and toxin binding means and the associated solid support. At the inlet and outlet ends are 80 micron nylon nets (18) for retaining the solid support within the container while allowing blood cells to pass through safely. The solid support comprises agarose particles (20), such as CN-Br activated Sepharose 6B available from Amersham Biosciences (Piscataway, N.J.). Anti-bacterial antibodies and anti-bacterial toxin antibodies (22) are affixed to the agarose support by conventional means according to instructions from the manufacturer using sterile solution and glassware that has been previously sterilized. For example, in the case of an EBTR unit for severe anthrax infection, once can use affinity-purified goat anti *bacillus anthracis* antibodies and goat anti *bacillus anthracis* toxin antibodies available from Scantibodies Laboratory, Inc. (Santee, Calif.).

Production of *Bacillus Anthracis* Antibodies

To create affinity purified anti *bacillus anthracis* polyclonal antibodies, one first uses killed *bacillus anthracis* available from the Centers for Disease Control (Atlanta, Ga.) as the immunogen for injection into the animal (typically a goat). The killed organism is suspended in a solution of 0.85 M sodium chloride to become the aqueous immunogen for injection. The aqueous immunogen for injection is mixed with an equal volume of Freund's complete adjuvant (a mixture of light mineral oil and mannide monooleate and inactivated *mycobacterium tuberculosis bacilli*). The resulting mixture is homogenized to produce an aqueous/oil emulsion for injection into the animal for the primary immunization. The immunogen dose is approximately 100-500 micrograms of *bacillus anthracis*. The goats are injected monthly with the same dose of immunogen complex except no *mycobacterium tuberculosis bacilli* is used in these subsequent injections. The goats are bled monthly under sterile conditions, starting approximately three months after the primary immunization. The serum (or antiserum) is derived from each bleeding by separating under sterile conditions the red blood cells from the blood by centrifugation and removing the antiserum, rich in antibodies against the *bacillus anthracis*.

To purify the antiserum for the desired antibody against *bacillus anthracis*, one packs a chromatography separation column with heat killed *bacillus anthracis* bound to cross linked agarose beads (such as CN-Br activated Sepharose 4B from Amersham Bioscience, Piscataway, N.J.) according to the instructions from the manufacturer using the sterile solutions and glassware that has been previously sterilized. The column (which also has been previously sterilized) is packed with the *bacillus anthracis* bound to agarose and the column is washed and equilibrated with sterile 0.01 M phosphate buffered saline (PBS). The antiserum is 0.22 micron filtered and loaded onto the column and washed with sterile 0.01 M PBS in order to remove the antibodies that are not against *bacillus anthracis*. The bound specific goat anti *bacillus anthracis* polyclonal antibody is eluted from the solid phase *bacillus anthracis* in the column by passing an elution solution of sterile 0.1 M glycine hydrochloride buffer, pH 2.5 through the column. The eluted polyclonal antibody is neutralized after it leaves the column with either the addition of sterile 1 M phosphate buffer, pH 7.5 or by buffer exchange with sterile 0.01 M PBS under sterile conditions, as is know to those of skill in the art. This affinity-purified goat anti *bacillus*

*anthracis* polyclonal antibody is further 0.22 micron filtered and stored at 2-8 degrees centigrade.

One can repeat the above procedure so as to make affinity-purified goat antibodies against the associated *bacillus anthracis* toxins, namely, protective antigen, edema factor, lethal factor, edema toxin and lethal toxin.

The affinity purified goat anti *bacillus anthracis* antibodies are bound to cross linked agarose beads (CN-Br activated Sepharose 6B which is available from Amersham Bioscience, Piscataway, N.J.) according to instructions from the manufacturer using sterile solutions and glassware that has been previously sterilized.

Production of an EBTR Unit

One can produce an EBTR unit suitable for use with a patient or domesticated animal in the following manner. A 200 ml glass chromatography column with inlet and outlet connectors and 80 micron nets at both inlet and outlet ports is sterilized. Sterile medical grade silicone tubing is attached to both the inlet and outlet of the column. A sterile shutoff valve is attached to the inlet tubing and a blood administration set with shutoff valve is attached to the outlet tubing. Needles (14 gauge) are attached to the ends of the inlet and outlet tubing. One gram of the affinity-purified goat anti *bacillus anthracis* bound to 200 ml of Sepharose 6B agarose beads is packed into the column. A peristaltic pump is attached onto the inlet tubing and the column is washed with sterile saline. With the sterile saline in place in the inlet and outlet tubing and the column, the shutoff valves are closed and the sterile unit is sealed under sterile conditions. An EBTR unit to remove products of the *bacillus anthracis* (i.e. toxins) is made by filling the column with goat antibodies to *bacillus anthracis* toxins (PA, EF, of LF) are bound to agarose beads (produced in a manner analogous to the goat anti *bacillus anthracis* antibodies described above). Typically, a 200 ml EBTR unit is capable of removing about one gram of an infecting bacterium.

Patient Selection for the Use of an EBTR Unit

Often a patient having a peripheral bacterial infection is not clinically diagnosed until the infection progresses into a severe peripheral bacterial infection. While it is possible to use an EBTR unit soon after a bacterial infection occurs, practically, in most cases the infection will not be identified until it is severe. For example, a *bacillus anthracis* infected patient typically will have passed into the secondary phase of infection by the time of diagnosis, and as such, is a candidate for the present invention. Candidacy can also be made by employing a rapid quantitative assay of the blood level for a particular infecting agent, such as *bacillus anthracis* and/or quantitative rapid tests for the toxic byproducts of the infecting agent, for *bacillus anthracis*, namely protective antigen, edema factor, lethal factor, edema toxin and lethal toxin. These rapid assays have the advantage of providing objective quantitation to the process of selecting patients for treatment. The selection process using the quantitative rapid test for *bacillus anthracis* can be based on a fairly low level of infecting bacteria. The administration of bacteriocidal antibiotics can bring about the accelerated release of life threatening toxins, i.e., the patient can die from toxin loads, even if the bacteria has been substantially reduced or effectively eliminated. The selection process using the quantitative rapid test for the products of *bacillus anthracis* is based on the critical life threatening threshold level of toxins already in the patient's blood. As in the case of establishing LD50 (lethal dose at which 50% of a population would die) one can determine separate threshold cutoff's for differing infections.

Treating a Patient with an EBTR Unit

Before using the EBTR unit such as described above, a patient is injected with about 100 units per kilogram of patient body weight of sodium heparin, available from Wyeth-Ayerst (Philadelphia, Pa.). To use the EBTR unit, the container is removed from its sterile sealed packaging and the inlet silicone tubing is connected to a blood peristaltic pump capable of delivering 100-300 ml per minute of blood, available from Baxter Healthcare (Deerfield, Ill.). The patient is placed in a supine position and both of the points of entry for the arm brachial veins are wiped with appropriate sterilant. The bottom inlet needle is inserted into one of the brachial veins of the patient and the pump speed is increased to 50 ml/min to allow blood to fill from the bottom of the EBTR unit. The EBTR unit is rotated to assure that no air is trapped in the unit. When blood has filled the EBTR unit and the blood administration set and with no air in the outlet line, the 14 gauge outlet line needle is inserted into the patient's other brachial vein. The pump speed is increased to 300 ml/min. During the EBTR treatment the patient's levels of *bacillus anthracis* and the levels of the products of *bacillus anthracis* are quantitatively assessed by quantitative rapid tests.

During the EBTR treatment, rapid quantitative tests can be used to assay blood levels of *bacillus anthracis* and levels of *bacillus anthracis* toxins. Typically, one would not treat the patient with antibiotics while using the EBTR unit, so as to avoid the release of further toxins into the peripheral system. The use of EBTR treatment can be halted when the infection and toxin levels have reached a point where the use of antibiotics will not set the patient at risk from subsequent release of *bacillus anthracis* toxins. One should note that one does not have to remove substantially all infecting bacterium or bacterial toxins from the patient, though this is preferable. Alternatively, one can discontinue EBTR treatment when the levels are low enough that typically the patient's immune system is able to overcome immunologically residual *bacillus anthracis* levels and clear the associated toxins naturally. Of course, such a decision should be made by the attending physician and is specific for each patient, depending upon numerous known factors. Due to the potential infectious nature of anthrax, the used EBTR unit is incinerated.

The ordinarily skilled artisan can appreciate that the present invention can incorporate any number of the preferred features described above.

All publications or unpublished patent applications mentioned herein are hereby incorporated by reference thereto.

Other embodiments of the present invention are not presented here which are obvious to those of ordinary skill in the art, now or during the term of any patent issuing from this patent specification, and thus, are within the spirit and scope of the present invention.

I claim:

1. A device for treating a patient having a peripheral bacterial infection, wherein the device comprises:

at least one adsorption container having an inlet means and an outlet means, where the inlet means and outlet means allow the patient's blood, in a whole or separated form, to be circulated through the adsorption container;

a first binding means associated with a solid support, wherein the first binding means is specific for affixing an infecting bacterium that is causing the severe peripheral bacterial infection, and the solid support is disposed and confined within the adsorption container;

thereby allowing for the removal of at least a portion of the infecting bacterium when the patient's blood is circulated through the adsorption container.

2. The device of claim 1 wherein the solid support has a surface area to volume ratio of at least about 4 to 1.

3. The device of claim 1 wherein the solid support is selected from the group consisting of coated beads, hollow fibers, and membranes.

4. The device of claim 1 wherein the first binding means is present in an amount sufficient to remove at least 1 mg of infecting bacteria.

5. The device of claim 1 wherein the first binding means is adsorbed or bonded to the solid support.

6. The device of claim 1 wherein the infecting bacterium is a *bacillus, meningococcus, streptococcus, staphylococcus*, or *paratuberculosis* species.

7. The device of claim 6, wherein the infecting bacterium is an antibiotic resistant bacterium.

8. The device of claim 7, wherein the antibiotic resistant bacterium is a *staphylococcus* species.

9. The device of claim 1 further comprising a second binding means,
    wherein the second binding means is associated with a solid support that is disposed and confined within an adsorption container, which may be the same adsorption container in which the first binding means is confined or it may be a separate adsorption container,
    and wherein the second binding means is specific for affixing at least one toxin produced by an infecting bacterium that is causing the severe peripheral bacterial infection,
    thereby allowing for the removal of at least a portion of the toxin and a portion of the infecting bacterium when the patient's blood is circulated through the adsorption container or adsorption containers.

10. The device of claim 9 wherein the first binding means and the second binding means are associated with the same solid support.

11. The device of claim 9 wherein the first binding means and the second binding means are both confined in a single adsorption container.

12. The device of claim 9 wherein the first and second binding means are confined in separate adsorption containers.

13. The device of claim 9 wherein the second binding means is present in an amount sufficient to remove at least 1 μg of toxin and the first binding means is present in an amount sufficient to remove at least 1 mg of infecting bacterium.

14. The device of claim 9, wherein the infecting bacterium is an antibiotic resistant bacterium.

15. The device of claim 9, wherein the antibiotic resistant bacterium is a *staphylococcus* species.

16. A method for treating a patient having a severe peripheral bacterial infection, the method comprising circulating the patient's blood, in whole or separated form, through an adsorption container and returning the treated blood to the patient,
    wherein the adsorption container comprises an inlet means and an outlet means to allow blood to circulate through the adsorption container;
    a solid support is disposed and confined within the adsorption container;
    and a first binding means that is specific for affixing an infecting bacterium that is causing the severe peripheral bacterial infection is associated with the solid support;
    thereby removing at least a portion of the infecting bacterium from the patient's blood when the blood is circulated through the adsorption container;
    wherein an antibiotic treatment of the patient is curtailed until the infecting bacterial load has been lowered to an acceptable risk level.

17. The method of claim 16 wherein the blood is circulated through the adsorption container until the bacterial load has been reduced to a level such that the use of an antibiotic does not put the patient at a significant risk of induced bacteremia or septicemia.

18. The method of claim 16 also comprising using a pump means to circulate the blood through the adsorption container.

19. The method of claim 16 in which the blood is monitored for the reduction in the level of bacteria.

20. The method of claim 16 wherein the infecting bacterium is a *bacillus, meningococcus, streptococcus, staphylococcus*, or *paratuberculosis* species.

21. The method of claim 20, wherein the infecting bacterium is an antibiotic resistant bacterium.

22. The method of claim 21, wherein the antibiotic resistant bacterium is a *staphylococcus* species.

23. The method of claim 16, wherein the adsorption container further comprises a second binding means,
    wherein the second binding means is associated with a solid support that is disposed and confined within an adsorption container, which may be the same adsorption container in which the first binding means is confined or it may be a separate adsorption container,
    and wherein the second binding means is specific for affixing at least one toxin produced by an infecting bacterium that is causing the severe peripheral bacterial infection,
    thereby allowing for the removal of at least a portion of the toxin and a portion of the infecting bacterium when the patient's blood is circulated through the adsorption container or adsorption containers.

24. The method of claim 23 wherein the infecting bacterium is a *bacillus, meningococcus, streptococcus, staphylococcus*, or *paratuberculosis* species.

25. The method of claim 24, wherein the infecting bacterium is an antibiotic resistant bacterium.

26. The method of claim 25, wherein the antibiotic resistant bacterium is a *staphylococcus* species.

* * * * *